United States Patent
Corcoran

(10) Patent No.: US 6,460,006 B1
(45) Date of Patent: Oct. 1, 2002

(54) SYSTEM FOR PREDICTING COMPACTION PERFORMANCE

(75) Inventor: Paul T. Corcoran, Washington, IL (US)

(73) Assignee: Caterpillar Inc, Peoria, IL (US)

( * ) Notice: Subject to any disclaimer, the term of this patent is extended or adjusted under 35 U.S.C. 154(b) by 0 days.

(21) Appl. No.: 09/237,161

(22) Filed: Jan. 25, 1999

Related U.S. Application Data

(60) Provisional application No. 60/113,439, filed on Dec. 22, 1998.

(51) Int. Cl.$^7$ .............................. G01N 9/36; G06F 15/00
(52) U.S. Cl. ........................ 702/137; 404/72; 404/122; 404/117
(58) Field of Search ................................. 702/137, 182; 700/174, 183, 184, 187; 73/78, 573, 579; 404/72, 122, 103, 117

(56) References Cited

U.S. PATENT DOCUMENTS

| | | | |
|---|---|---|---|
| 4,467,652 A | | 8/1984 | Thurner et al. ............... 73/573 |
| 4,979,197 A | | 12/1990 | Troxler, Sr. et al. |
| 5,177,415 A | * | 1/1993 | Quibel et al. ............... 318/128 |
| 5,471,391 A | | 11/1995 | Gudat et al. |
| 5,493,494 A | * | 2/1996 | Henderson ................... 701/50 |
| 5,942,679 A | | 8/1999 | Sandstrom |
| 6,122,601 A | * | 9/2000 | Swanson et al. ............ 702/137 |

FOREIGN PATENT DOCUMENTS

| | | | |
|---|---|---|---|
| DE | 3421824 A1 | 12/1985 | |
| DE | 297 23 171 U1 | 4/1998 | |
| FR | 0 761 886 A1 | 3/1997 | |
| RU | 1761864 A1 | 3/1990 | ............. E02D/1/00 |
| RU | 1806244 A3 | 8/1990 | ............. E02D/1/00 |
| WO | WO9425680 | 11/1994 | |

OTHER PUBLICATIONS

Article: MBW Compaction Meter—Quality control for soil compaction MBW Inc., P.O. Box S78—250 Hartford Rd. Slinger WI 53086–0378.

Article: bauma 98; GPB For Compaction Control.

* cited by examiner

*Primary Examiner*—John S. Hilten
*Assistant Examiner*—Demito Pretlow
(74) *Attorney, Agent, or Firm*—Steve G Kibby

(57) ABSTRACT

Compaction performance follows a well behaved response curve for a particular material condition/compaction machine combination. Accordingly, a compaction response curve is determined from measured values representative of material density after a first and second pass by a compaction machine. The response curve is used to predict the number of passes required by the compaction machine to reach a desired density for the material, and thereby avoid making unneeded additional machine passes or passes which would not be effective due to diminished returns. The system may provide an indication when required compaction will not be achieved or will require an excessive number of passes, i.e. such as happens when moisture content of the material is high.

15 Claims, 2 Drawing Sheets

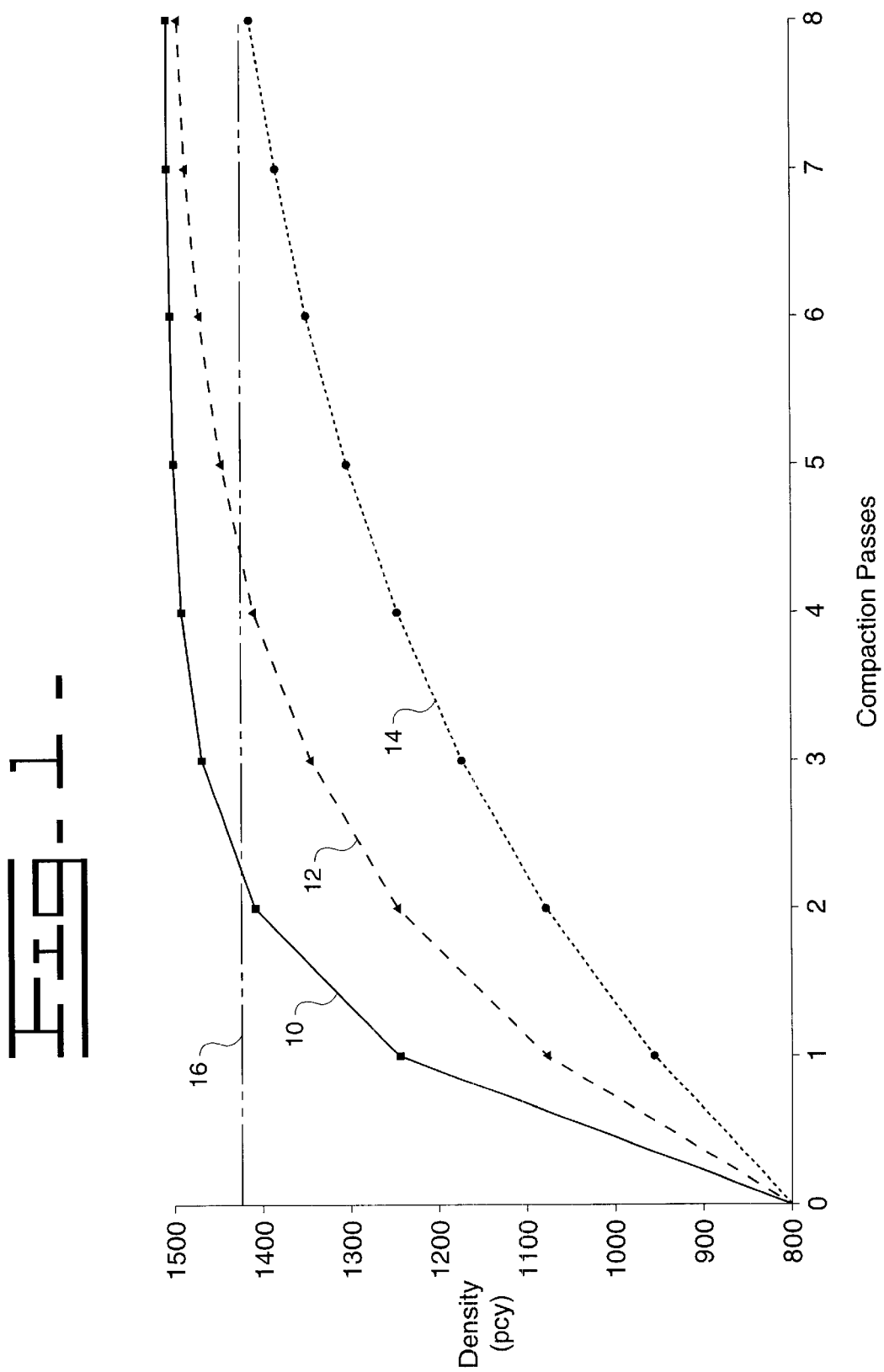

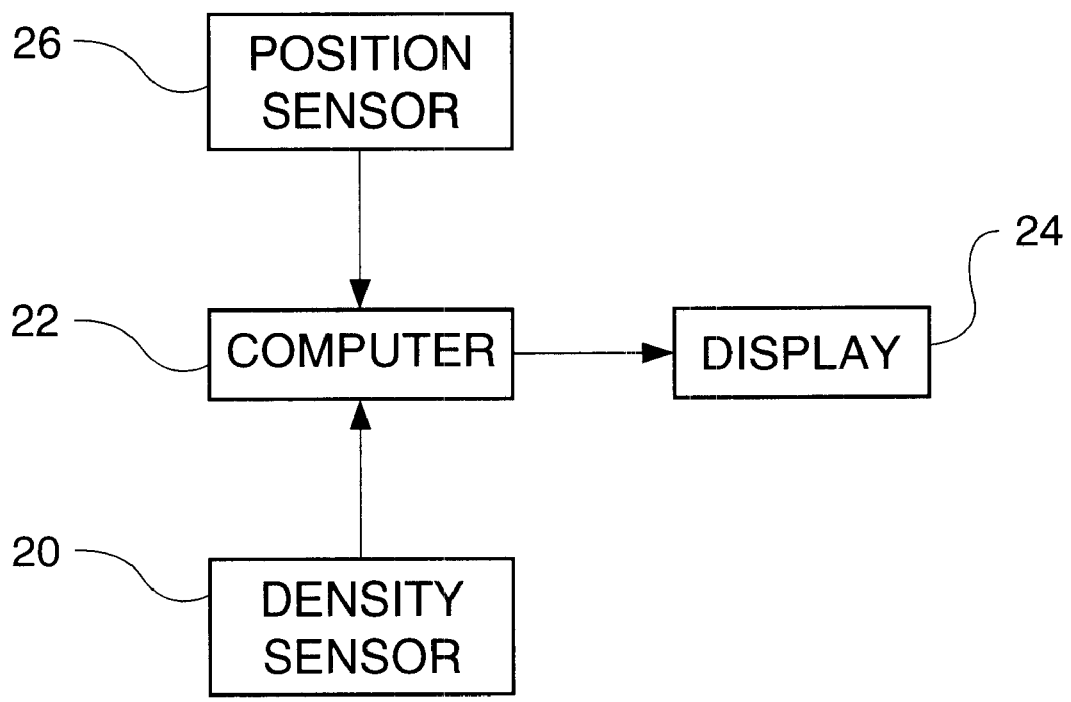

SYSTEM FOR PREDICTING COMPACTION PERFORMANCE

This application claims the benefit of prior provisional patent application Ser. No. 60/113,439 filed Dec. 22, 1998.

TECHNICAL FIELD

This invention relates to a system for monitoring compaction of material by a work implement, and more particularly to an information system for compaction machinery which measures compaction density on a first few passes to predict the number of compaction passes needed to meet specification.

As used in this patent specification the phrase "compaction machine" and various approximations thereof refer to self-propelled mobile machines such as landfill, earth and asphalt compactors which are provided with a prime mover (for example an engine) on a carriage to drive rotating elements such as wheels or rollers serving as both carriage support and the compacting tool.

BACKGROUND ART

Despite the development of sophisticated and powerful compacting machinery it remains a time consuming and labor intensive chore to adequately compact material such as earth or asphalt at work sites such as construction sites, roads and the like. The material to be compacted is typically spread over the site in an uncompacted state and must be repeatedly traversed by a compaction machine until it is compressed to a desired degree of compaction. A common type of compacting machinery includes one or more heavy compacting wheels or rollers which compact the material in their path.

Compacting operations are still largely monitored and controlled by the machinery operators and supervisors on an intuitive basis, or by estimating results from laboratory information about the type of material being compacted. For example, a number of compaction passes required over a specific site material may be empirically determined or established by contract or local regulation. The number of passes is generally very conservatively selected to satisfy a range of environmental and material conditions, often resulting in unproductive passes over material already meeting the density specifications.

There have been several efforts to electronically provide the operator with detailed information regarding the real-time progress being made in the compaction operation. In U.S. Pat. No. 5,471,391, Gudat et al. disclose maintaining a detailed dynamic site model by precisely determining in three dimensional space the location of the compacting portions of the machine relative to the site. Information indicative of compaction, such as the number of passes a compacting wheel makes over a given area or elevational change from the uncompacted level, are automatically determined by continuously updating the site model.

Vibratory compactors typically utilize a drum having a mass eccentrically rotating at a rate near a resonance frequency of the compacted material to increase its density. In U.S. Pat. No. 5,177,415, Quibel et al. disclose continuously evaluating the degree of compaction of a material provided by vibrating compaction tool through calculation of the total applied static, dynamic and centrifugal forces.

In U.S. Pat. No. 4,979,197, Troxler, Sr. et al. disclose a device mounted to a compaction machine in a spaced apart relation from the surface to emit nuclear radiation and counting photons back scattered from the material. An ultrasonic transducer or laser measuring the air gap purportedly permits accurate compensation therefor in a density determination. The machine is equipped with a pair of signal lights to indicate whether or not a desired degree of compaction has been reached.

Although each of the foregoing are individually intended to provide an operator with information to improve compaction efficiency, there continues to be a need to increase the safety and reliability of the compaction measurement, and in some cases provide additional information useful for compaction of the material.

The present invention is directed to overcoming one or more of the disadvantages set forth above.

DISCLOSURE OF THE INVENTION

Compaction performance follows a well behaved response curve for a particular material condition/compaction machine combination. According to one aspect of the present invention, compaction performance is predicted using a compaction response curve determined from measured values values representative of material density after a first and second pass by a compaction machine. The response curve is used to predict the number of passes required by the compaction machine to reach a desired density for the material.

Other details, objects and advantages of the invention will become apparent as certain present embodiments thereof and certain present preferred methods of practicing the same proceeds.

BRIEF DESCRIPTION OF THE DRAWINGS

A more complete appreciation of this invention may be had by reference to the following detailed description when considered in conjunction with the accompanying drawings in which like reference symbols indicate the same or similar components, wherein:

FIG. 1 is a graphical illustration of various compaction response curves for a material;

FIG. 2 is a schematic illustration of information and control elements useful for practicing the present invention.

BEST MODE FOR CARRYING OUT THE INVENTION

Turning now to the drawings and referring first to FIG. 1, three different response curves illustrating the increase in density after successive passes by a compaction machine are illustrated. For a given type of material to be compacted, the compaction density follows a well behaved response curve according to the relationship:

$$\gamma_n = c(1 - e^{-n/k}) \qquad \text{Equation 1}$$

where n is the number of passes, c is a constant related to the maximum density to which the material will compact, and k is the inflection point of the response curve.

Of course, a material does not begin with a density of zero, therefore the foregoing relationship is preferably utilized in the form:

$$\gamma_n = \gamma_0 + (\gamma_{max} - \gamma_0)(1 - e^{-n/k}) \qquad \text{Equation 2}$$

where $\gamma_0$ is the starting density and $\gamma_{max}$ is the predicted maximum density.

As can be seen from the illustration in FIG. 1, the density $\gamma_n$ increases less rapidly with each succeeding pass of the machine, as it approaches the maximum density. The rapidity with which the density increases will vary, depending on the material properties and the efficiency of the compaction machine, but will nonetheless increase predictably according to the foregoing relationship. In FIG. 1 for example, a soil having an initial density of 800 pounds/cubic yard and a maximum density of 1500 pcy may compact along curve 10, 12 or 14, depending on the inflection k of one, two or four, respectively.

Once the response curve of a particular material/machine combination can be determined, it becomes possible, using measured data representative of density from only a few passes, to predict the result of further compaction passes. According to one aspect of the present invention, the compaction process is stopped upon determining that additional machine passes are not needed or would not be effective due to diminished returns.

By way of example, a construction specification may call for final density $\gamma_{spec}$ of 95% of a standard maximum dry density empirically determined in a laboratory for that material.

In order to determine a response curve for a particular material/machine combination, a value representative of density is measured before and after a first and a second machine pass (although not necessarily the first and second passes). The measured values are input into the foregoing equation to solve for the constants k and $\gamma_{max}$, whereupon a desired density may be plugged into the equation using those constants to solve for the pass number n at which that density will be reached.

By way of example, a construction specification may call for final density $\gamma_{spec}$ of 95% of a standard maximum dry density empirically determined in a laboratory for that material. FIG. 1 depicts a horizontal line 16 at 95% of an exemplary maximum dry density of 1500 pcy. If the measured density data were to indicate a response corresponding to curve 10, a system according to the present invention would predict $\gamma_{spec}$ would be reached after the third pass, whereas a response curve 12 would predict five passes will be required.

Turning to FIG. 2, a system for predicting compaction performance according to the present invention includes an element for providing a value indicative of material density, preferably a density sensor 20 located on the compaction machine proximate a material to be compacted. Various types of density sensors are known, such as a Troxler monitor utilizing back-scattered radiation or piezo-electric sensing of a pressure wave. Alternatively, a value indicative of density could be indirectly derived from a compaction machine parameter, such acceleration along an axis of a vibrating drum compactor or rolling resistance, and converted to a density measurement.

An initial density and a density measured after at least a first and second compaction pass at a site are provided to a computer 22, along with a desired final density, to predict the number of passes required to achieve the desired density as described above. The predicted number of passes may be output on a display 24, such as a Liquid Crystal Display, to enable the operator to refine his compaction planning on the basis of a predicted completion pass.

Industrial Applicability

On a large area of compaction it might be determined that part of the area will require different numbers of machine passes to achieve required compaction. For example, the material may not be homogenous throughout the site. In such a case, the site can be divided into a number of regions, such that a response curve is determined for each region. A position sensor 26, such as an inertial sensor, scaling wheel, or the like may be provided to automatically indicate to the computer 22 a region in which the compaction machine is located, or the operator may manually associate a density measurement with a defined region such as by electrical switches. According to one embodiment of the invention, the site may be mapped into a multiplicity of cells, each having its own calculated response curve, using a global positioning satellite (GPS) receiver such as in the manner set forth in the Gudat patent mentioned herein by way of background. This can then be used to plan the traffic pattern for the compactor.

Another useful aspect of the present invention illustrated as curve 14 in FIG. 1, would be where the predicted response curve indicates required compaction will not be achieved or will require an excessive number of passes, i.e. such as happens when moisture content of the material is high. One alternative method to check for such a situation is to compare the predicted maximum density determined for a response curve to the desired density set forth in the specifications.

If the specification exceeds the calculated predicted maximum, or if the predicted number exceeds some maximum desirable number of passes, a warning indication may be provided to display 24. The compaction process can then be stopped and soil checks performed to determine changes in the construction process, such as disking the soil to facilitate drying, or if possible utilizing a more efficient compaction machine configuration.

While certain present preferred embodiments of the invention and certain present preferred methods of practicing the same have been illustrated and described herein, it is to be distinctly understood that the invention is not limited thereto but may be otherwise variously embodied and practiced within the scope of the following claims.

What is claimed is:

1. A method for predicting compaction performance, comprising the steps of:

measuring values representative of material density after at least a first and second pass by a compaction machine;

determining a compaction response curve from said measured values; and predicting from said response curve a number of successive passes by the compaction machine over the material required to reach a desired density for the material.

2. A method as set forth in claim 1, further comprising performing said predicted number of passes to compact the material.

3. A method as set forth in claim 1, said step of determining a compaction response curve further comprising computing a predicted maximum density and an inflection point defining said curve.

4. A method as set forth in claim 3, further comprising comparing said predicted maximum density to a desired final density to determine whether the desired density can be achieved within a reasonable number of passes.

5. A method as set forth in claim 1, said step of measuring values comprising sensing the density of the material using a sensor located on the compaction machine proximate the material to be compacted.

6. A method as set forth in claim 1, said step of measuring values comprising deriving a density measurement from a compaction machine parameter.

7. A method as set forth in claim 6, wherein said machine parameter is one of acceleration along an axis of a vibrating drum compactor and rolling resistance.

8. A method as set forth in claim 1, further comprising:

defining a plurality of regions within a compaction site;

determining a compaction response curve from measured values from each said region; and predicting from a corresponding said response curve a number of passes by the compaction machine required to reach a desired density for the material in each said region.

9. A system for predicting compaction performance, comprising:

means for measuring values representative of material density after at least a first and second pass by a compaction machine;

computing means for determining a compaction response curve from said measured values, and for predicting from said response curve a number of successive passes by the compaction machine over the material required to reach a desired density for the material; and means for displaying said number of passes.

10. A system as set forth in claim 9, further comprising said computing means computing a predicted maximum density and an inflection point defining said curve.

11. A system as set forth in claim 10, further comprising said determining means comparing said predicted maximum density to a desired final density to determine whether the desired density can be achieved within a reasonable number of passes.

12. A system as set forth in claim 9, said measuring means comprising a using a sensor located on the compaction machine proximate the material to be compacted.

13. A system as set forth in claim 9, said measuring means comprising a Troxler meter.

14. A system as set forth in claim 9, said measuring means comprising an accelerometer measuring acceleration along an axis of a vibrating drum compactor.

15. A system as set forth in claim 9, further comprising:

position sensing means for determining a location of the compaction machine within one of a plurality of regions within a compaction site; and wherein said computing means determines a compaction response curve from measured values from each said region, and predicts from a corresponding said response curve a number of passes by the compaction machine required to reach a desired density for the material in each said region.

* * * * *